US00PP18447P2

(12) United States Plant Patent
Iwaki et al.

(10) Patent No.: US PP18,447 P2
(45) Date of Patent: Jan. 22, 2008

(54) ***ANTIRRHINUM* PLANT NAMED 'SUNKISUPIN'**

(50) Latin Name: ***Antirrhinum majus*×*Antirrhinum hispanicum***
Varietal Denomination: Sunkisupin

(75) Inventors: Kazunari Iwaki, Shiga (JP); Tomoya Misato, Yamanashi (JP); Yasunori Yomo, Kanagawa (JP)

(73) Assignee: Suntory Flowers Ltd., Tokyo (JP)

( * ) Notice: Subject to any disclaimer, the term of this patent is extended or adjusted under 35 U.S.C. 154(b) by 0 days.

(21) Appl. No.: 11/509,538

(22) Filed: Aug. 24, 2006

(51) Int. Cl.
*A01H 5/00* (2006.01)

(52) U.S. Cl. ..... Plt./322

(58) Field of Classification Search ..... Plt./322
See application file for complete search history.

*Primary Examiner*—Kent Bell
*Assistant Examiner*—S. B. McCormick-Ewoldt
(74) *Attorney, Agent, or Firm*—C. A. Whealy

(57) ABSTRACT

A new and distinct cultivar of *Antirrhinum* plant named 'Sunkisupin', characterized by its upright and mounded plant habit; freely branching habit and short internodes; dense and bushy plant form; numerous dark pink-colored flowers; and long flowering period.

1 Drawing Sheet

Botanical designation: *Antirrhinum majus*×*antirrhinum hispanicum.*
Cultivar denomination: 'Sunkisupin'.

CROSS-REFERENCED TO RELATED APPLICATIONS

Title: *Antirrhinum* Plant Named 'Sunkisupapu'; filed concurrently First Named Applicant: Kazunari Iwaki

BACKGROUND OF THE INVENTION

The present invention relates to a new and distinct cultivar of *Antirrhinum*, botanically known as *Antirrhinum majus*× *Antirrhinum hispanicum* and hereinafter referred to by the name 'Sunkisupin'.

The new *Antirrhinum* is a product of a planned breeding program conducted by the Inventors in Shiga, Japan. The objective of the breeding program is to create new freely flowering potted *Antirrhinums.*

The new *Antirrhinum* originated from a cross-pollination in Shiga, Japan in May, 2002 of a proprietary selection of *Antirrhinum majus*×*Antirrhinum hispanicum* identified as code number His13-4, not patented, as the female, or seed, parent with a proprietary selection of *Antirrhinum majus*× *Antirrhinum hispanicum* identified as code number His13-2, not patented. The cultivar Sunkisupin was discovered and selected by the Inventors as a flowering plant from within the progeny of the stated cross-pollination in a controlled environment in Shiga, Japan.

Asexual reproduction of the new *Antirrhinum* by cuttings in a controlled environment in Shiga, Japan since November, 2005, has shown that the unique features of this new *Antirrhinum* are stable and reproduced true to type in successive generations.

SUMMARY OF THE INVENTION

The cultivar Sunkisupin has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Sunkisupin'. These characteristics in combination distinguish 'Sunkisupin' as a new and distinct cultivar of *Antirrhinum:*

1. Upright and mounded plant habit.
2. Freely branching habit and short internodes; dense and bushy plant form.
3. Numerous dark pink-colored flowers.
4. Long flowering period.

Plants of the new *Antirrhinum* differ from plants of the parent selections primarily in flower size as plants of the new *Antirrhinum* have larger flowers than plants of the parent selections.

Plants of the new *Antirrhinum* differ from plants of the cultivar Sunkisupapu, U.S. Plant Patent application filed concurrently, primarily in flower color.

Plants of the new *Antirrhinum* can be compared to plants of the cultivar Festa Pink, not patented. Plants of the new *Antirrhinum* and the cultivar Festa Pink differ in the following characteristics:

1. Plants of the new *Antirrhinum* are taller and broader than plants of the cultivar Festa Pink.
2. Plants of the new *Antirrhinum* have longer and thicker lateral branches than plants of the cultivar Festa Pink.
3. Plants of the new *Antirrhinum* are more freely branching than plants of the cultivar Festa Pink.
4. Plants of the new *Antirrhinum* have smaller leaves than plants of the cultivar Festa Pink.
5. Plants of the new *Antirrhinum* have much longer inflorescences than plants of the cultivar Festa Pink.
6. Plants of the new *Antirrhinum* have lighter-colored flowers than plants of the cultivar Festa Pink.
7. Plants of the new *Antirrhinum* are more freely flowering than plants of the cultivar Festa Pink.

BRIEF DESCRIPTION OF THE PHOTOGRAPHS

The accompanying colored photographs illustrate the overall appearance of the new *Antirrhinum,* showing the colors as true as it is reasonably possible to obtain in colored reproductions of this type. Colors in the photographs may differ slightly from the color values cited in the detailed botanical description which accurately describe the colors of the new *Antirrhinum*.

The photograph at the top of the sheet comprises a side perspective view of a typical flowering plant of 'Sunkisupin' grown in a container.

The photograph at the bottom or the sheet is a close-up view of typical flowers of 'Sunkisupin'.

DETAILED BOTANICAL DESCRIPTION

The aforementioned photographs and following observations, measurements and values describe plants grown in Shiga, Japan, under commercial practice in a polyethylene-covered greenhouse with day temperatures ranging from 10° C. to 20° C. and night temperatures averaging 0° C. Plants had been growing for about four months in 15-cm containers when the photographs and description were taken. In the following description, color references are made to The Royal Horticultural Society Colour Chart, 2001 Edition, except where general terms of ordinary dictionary significance are used.

Botanical classification: *Antirrhinum majus*×*Antirrhinum hispanicum* cultivar Sunkisupin.

Parentage:

*Female, or seed, parent.*—Proprietary selection of *Antirrhinum majus*×*Antirrhinum hispanicum* identified as code number His 13-4, not patented.

*Male, or pollen, parent.*—Proprietary selection of *Antirrhinum majus*×*Antirrhinum hispanicum* identified as code number His 13-2, not patented.

Propagation:

*Type.*—By cuttings.

*Time to initiate roots.*—About 10 days at 20° C. to 25° C.

*Time to produce a rooted young plant.*—About 20 days at 20° C. to 25° C.

*Root description.*—Fine, fibrous and fleshy; white in color.

*Rooting habit.*—Freely branching.

Plant description:

*Plant form/habit.*—Upright and mounded plant habit; inverted triangle. Freely branching habit with short internodes; dense and bushy plant form; about 16 lateral branches develop per plant; pinching will enhance branching.

*Plant height.*—About 33.4 cm.

*Plant width* (*spread*).—About 24.8 cm.

*Lateral branches.*—Length: About 26.6 cm. Diameter: About 2.8 mm. Internode length: About 1 cm. Strength: Moderately strong. Texture: Smooth, glabrous. Color: 144A overlain with 165A.

Foliage description:

*Arrangement.*—Before flowering, opposite; after flowering, alternate; simple.

*Length.*—About 4.1 cm.

*Width.*—About 1.4 cm.

*Shape.*—Lanceolate.

*Apex.*—Acute to obtuse.

*Base.*—Cuneate.

*Margin.*—Entire.

*Texture, upper and lower surfaces.*—Smooth, glabrous.

*Venation pattern.*—Pinnate; reticulate.

*Color.*—Developing leaves, upper surface: 137C, towards the margins, N186A. Developing leaves, lower surface: 138B. Fully expanded leaves, upper surface: 137B; venation, 144A. Fully expanded leaves, lower surface: 146B; venation, 144A.

*Petiole.*—Length: About 4.2 mm. Diameter: About 1.4 mm. Texture, upper and lower surfaces: Smooth, glabrous. Color, upper and lower surfaces: 144A.

Flower description:

*Flower type/habit.*—Single bi-labiate flowers arranged in terminal and lateral racemes; flowers face obliquely upright to outward. Freely flowering habit with about 20 flowers per inflorescence and about 21 inflorescences develop per plant.

*Fragrance.*—None detected.

*Natural flowering season.*—Continuously flowering from early autumn until early summer in Japan. Flowers not persistent.

*Postproduction longevity.*—Flowers last about five days on the plant.

*Flower buds.*—Height: About 2.8 cm. Diameter: About 1 cm. Shape: Obovate. Color: 180D.

*Inflorescence height.*—About 20.3 cm.

*Inflorescence diameter.*—About 6.9 cm.

*Flower diameter.*—About 3.5 cm by 3.6 cm.

*Flower depth.*—About 4 cm.

*Petals.*—Quantity per flower: Upper lip, two-lobed; lower lip, three-lobed; petals fused at the base. Upper lip: Length: About 1.4 cm. Width: About 3.3 cm. Shape: Broadly obovate. Apex: Rounded. Margin: Entire. Texture, upper and lower surfaces: Smooth, glabrous; velvety. Color: When opening and fully opened, upper surface: Close to 55A; towards the throat, 54D. When opening and fully opened, lower surface: 55B. Lower lip: Length: About 1.4 cm. Width: About 3.6 cm. Shape: Obovate. Apex: Rounded. Margin: Entire. Texture, upper and lower surfaces: Smooth, glabrous; velvety. Color: When opening and fully opened, upper surface: 55A. When opening and fully opened, lower surface: 55B. Tube/throat: Length: About 1.8 cm. Diameter: About 1 cm. Texture, upper and lower surfaces: Sparsely pubescent. Color, tube and throat: 55B.

*Sepals.*—Quantity per flower: Typically five in a single whorl. Length: About 7.6 mm. Width: About 4 mm. Shape: Ovate. Apex: Acute. Margin: Entire. Texture, upper surface: Smooth, glabrous. Texture, lower surface: Pubescent. Color: When opening, upper surface: 144B. When opening, lower surface: 165A. Fully opened, upper surface: 144A. Fully opened, lower surface: N199A.

*Pedicels.*—Length: About 3.6 cm. Diameter: About 1.2 mm. Strength: Strong. Texture: Smooth, glabrous. Color, upper surface: 182B. Color, lower surface: 145B.

*Reproductive organs.*—Stamens: Quantity per flower: Typically four. Anther size: About 3 mm by 3 mm. Anther shape: Oval, bi-lobed. Anther color: 14C. Filament color: 65B. Pollen amount: Moderate. Pollen color: 9A. Pistils: Quantity per flower: One. Pistil length: About 1.8 cm. Stigma shape: Club-shaped. Stigma color: 197B. Style length: About 1.7 cm. Style color: 182C. Ovary color: 152D.

*Seed/fruit.*—Seed and fruit development have not been observed.

Disease/pest resistance: Plants of the new *Antirrhinum* have not been noted to be resistant to pathogens and pests common to *Antirrhinum*.

Garden performance: Plants of the new *Antirrhinum* have been observed to have good garden performance and tolerate rain, wind and temperatures ranging from about −10° C. to about 30° C.

It is claimed:

1. A new and distinct *Antirrhinum* plant named 'Sunkisu-pin' as illustrated and described.

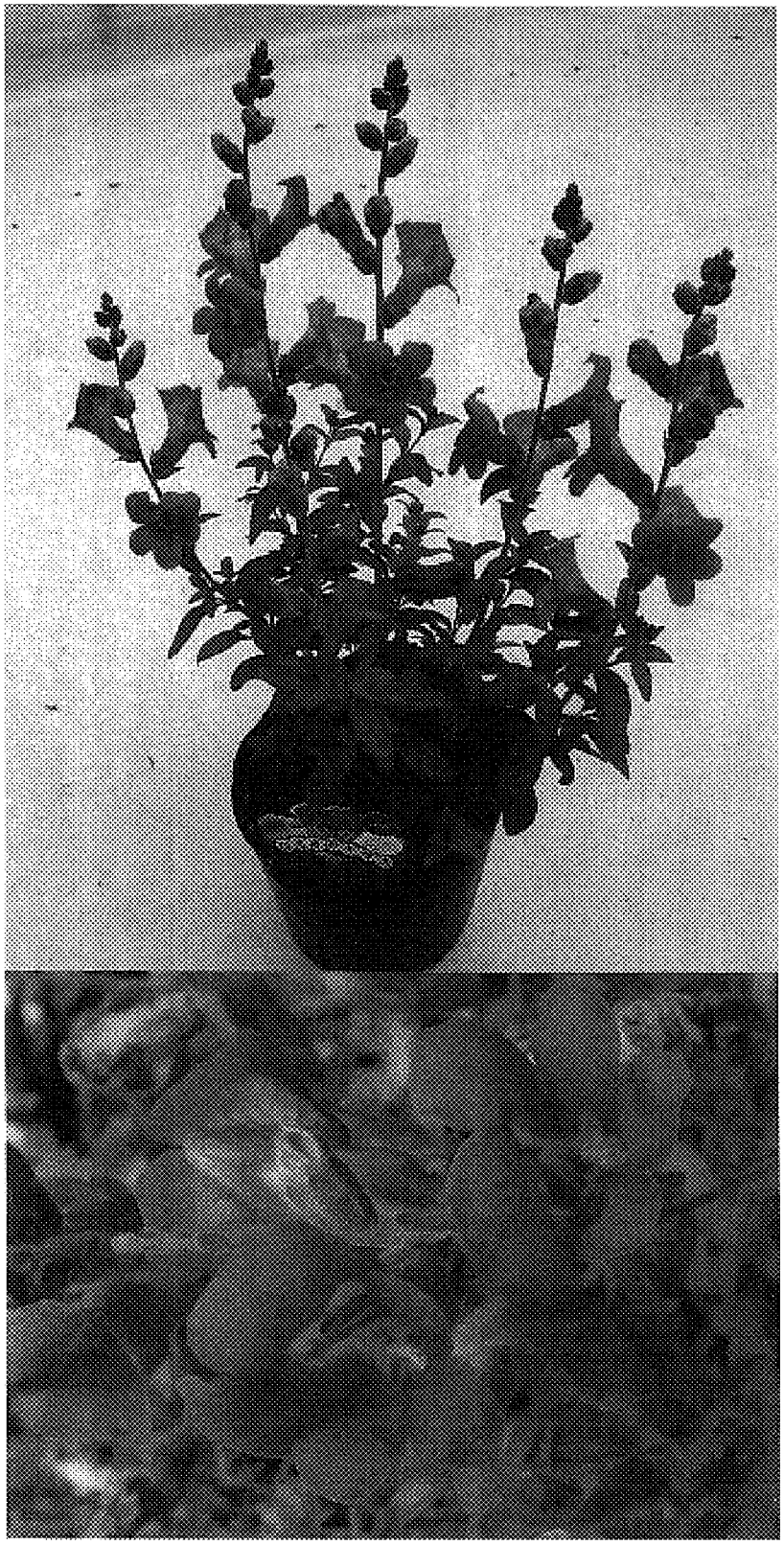

* * * * *